United States Patent [19]

Holtkamp, Sr.

[11] Patent Number: Plant 7,057

[45] Date of Patent: Nov. 21, 1989

[54] AFRICAN VIOLET PLANT NAMED FARRAH

[76] Inventor: Reinhold Holtkamp, Sr., Werther Strasse 112, D4294 Isselburg, Fed. Rep. of Germany

[21] Appl. No.: 262,594

[22] Filed: Oct. 26, 1988

[51] Int. Cl.[4] ..... A01H 5/00

[52] U.S. Cl. ..... Plt./69

[58] Field of Search ..... Plt. 69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Farrah characterized by its single dark pink flowers with slightly wavy edges and a darker center radiating somewhat into the petals; strong, upright flower stems that curve toward the center to form a compact bouquet above the leaves; dark green slightly serrated leaves, profuse flowering, vigorous growth habit, flowering 10-11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Farrah.

The new cultivar was referred to during the breeding and selection process by the designation H 5/2 and is a product of a planned breeding program. The new cultivar was originated from a cross made by me in the controlled breeding program in Haffen, Federal Republic of Germany. The female, or seed parent was a cultivar designated 69. The male, or pollen parent was a cultivar designated E 16/6.

Farrah was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Farrah has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Farrah, which in combination distinguish this African violet as a new and distinct cultivar;

(1) Strong, upright flower stems curving slightly toward the center.

(2) Single dark pink flowers with slightly wavy edges and a darker center radiating somewhat into the two smaller petals.

(3) Profuse flowering.

(4) Each plant has 7–8 and more upright flower stems each of which carries 7–9 flowers.

(5) Long lasting, non-dropping flowers.

(6) Vigorous grower.

(7) Plant saleable 10 toll weeks after potting.

(8) Seed capsules push slightly through.

(9) Dark green leaves.

(10) After maturity the flowers dry off, and remain on the peduncle without becoming infected by botrytis.

The closest known variety is West Virginia, whose leaf color and flower shape and flower color are similar to Farrah. Differences between West Virginia and Farrah are the darker pink color, the lack of a dark line on the edges and the lack of frilled edges of Farrah.

Accompanying color photographic drawing shows a typical specimen plant of the new cultivar. The colors appearing in the photograph are as true as possible with color illustrations of this type.

In the following description, color references are made to the Royal Hórticultural Society Colour Chart (RHS), except where general colors of ordinary significance are referred to. Color values were taken under natural sunlight conditions at approximately 2 p.m. in Nashville, Tenn.

ed

Botanical classification: *Saintpaulia ionantha,* Ramat., c.v. Farrah.

Parentage:

*Male parent.*—E 16/;6.

*Female parent.*—69.

Propagation: The new cultivar holds its distinguishing characteristics through successive propagations by leaf cuttings.

Plant: From 10 cm to 12 cm tall when grown in pots, and approximately 24–26 cm in diameter when fully grown.

*Leaves.*—General form: oval to spear-shaped. Diameter: 60–75 mm. Texture: Velvety. Aspect: Shiny, hairy, slightly serrated. Veins: Upperside: visible; underside: very well pronounced, light green, shiny. Color (upperside): Yellow-Green Group 147 A and darker. Color (underside): Greyed-Purple Group 183 D. Petiole: Strong upright, purplish green, hairy.

*Flowers.*—Buds: Ball-shaped, 7–9 mm just before opening, purplish pink. Sepals: Five(5). Colr: Green with purplish brown touch. Calyx: Shape: Funnel-shaped. Aspect: Spear-shaped, hairy. Peduncle: Character: Strong upright, hairy. Color: Purplish brown. Individual flowers: Size: 40–45 mm. Shape: Single violet-shaped (3 large and 2 small petals) with slightly wavy edges.

Color (upperside): Between Red-Purple Group 74 C and Red-Purple Group 66 C. Under cooler temperature and more intensive lighting, the pink tends to intensify. Color (underside): Red-Purple Group 74 D. Borne: Each flower stem carries 7–9 flowers on strong, upright peduncle that are free standing above the leaves, thereby forming a compact bouquet. Flowering habit: Flowers 10–11 weeks after potting.

*Reproductive organs.*—Stamens: Two (2) Anthers: 2 composed of 4 anther cells, seed capsule pushes slightly through. Filaments: Yellowish green with pink touch on edges, 4 mm long. Pollen Color: Yellow Group 7 A. Styles: 7 mm long, dark pink, base of ovary light green and hairy.

*Roots.*—Normally developed, white when young, turning slightly brownish when older.

Disease resistance: Good.

General observations: Farrah is a very attractive, vigorous grower with dark green, velvety and shiny leaves. A tight bouquet of single violet-shaped flowers free standing above the leaves develops after approximately 10–11 weeks. Each of the 7–8 and more strong flower stems carries 7–9 single dark pink flowers with slightly wavy edges. The pink color in the center is darker and radiates somewhat into the petals. Occasionally, 1–2 additional small petals may develop. The flowers are long-lasting and non-dropping and the seed capsules push slightly through.

I claim:

1. A new and distinct cultivar of African violet named Farrah, as described and illustrated, and particularly characterized by its single, dark pink flowers with slightly wavy edges and a darker center radiating somewhat into the petals; strong, upright flower stems that curve toward the center to form a compact bouquet above the leaves; dark green slightly serrated leaves; profuse flowering; vigorous growth habit flowering 10–11 weeks after potting, and its long lasting and non-dropping flowers.

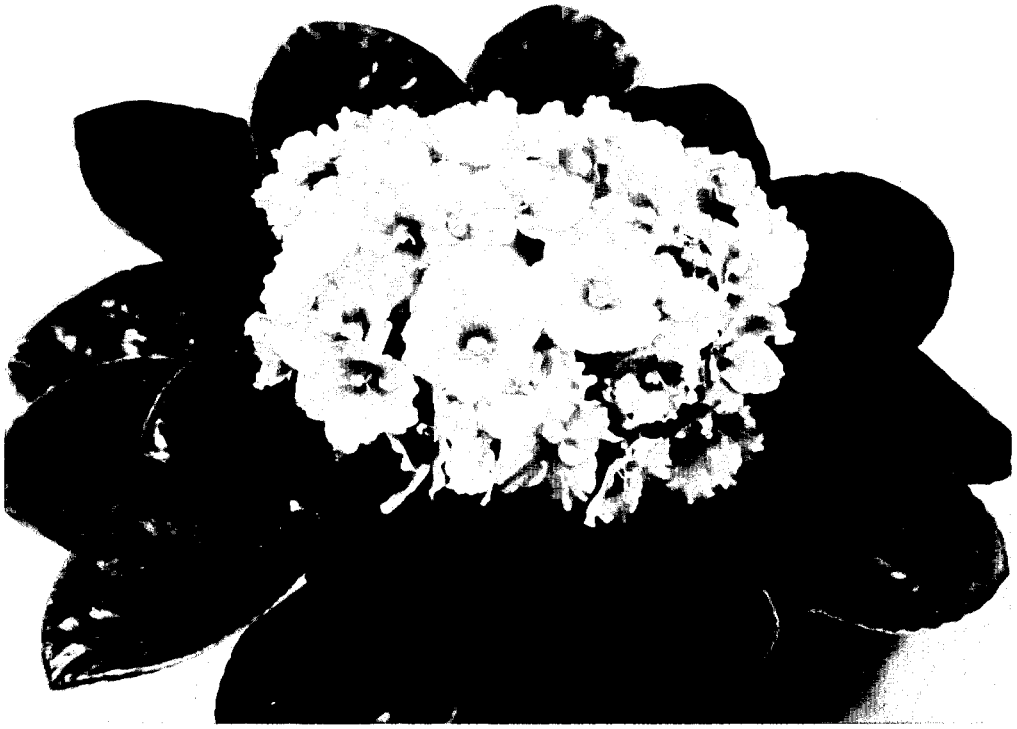

* * * * *